United States Patent [19]

Stuart et al.

[11] Patent Number: 4,818,693
[45] Date of Patent: Apr. 4, 1989

[54] METHODS AND MATERIALS FOR ENHANCED SOMATIC EMBRYO REGENERATION IN THE PRESENCE OF AUXIN

[75] Inventors: David A. Stuart; Steven G. Strickland, both of Davis, Calif.

[73] Assignee: Plant Genetics, Inc., Davis, Calif.

[21] Appl. No.: 888,239

[22] Filed: Jul. 21, 1986

Related U.S. Application Data

[63] Continuation of Ser. No. 504,891, Jun. 16, 1983, which is a continuation-in-part of Ser. No. 496,186, May 19, 1983.

[51] Int. Cl.⁴ .......................... C12N 5/00; C12N 5/02
[52] U.S. Cl. ............................ 435/240.49; 435/240.5; 435/240.51; 435/240.54
[58] Field of Search ...................... 435/240, 241, 240.4, 435/240.49, 240.5, 240.54; 47/58; 71/77, 92

[56] References Cited

PUBLICATIONS

Tazawa et al., 1969, Protoplasma 68: 157–173.
Walker et al., 1981, Plant Cell Tiss. Org. Cult. 1: 109–121.
Green et al., 1983, Miami Wint. Symp. 20: 147–157.
Wetherell et al., 1976, Physiol. Plant. 37: 97–103.
The Fifteenth Miami Winter Symposium, 17–21 Jan. 1983, Konover Hotel, Miami Beach, Fla., "Advances in Gene Technology: Molecular Genetics of Plants and Animals".

Primary Examiner—Charles F. Warren
Assistant Examiner—David Fox
Attorney, Agent, or Firm—Limbach, Limbach & Sutton

[57] ABSTRACT

Methods and compositions are provided to improve the quantity of embryos obtained by induction of somatic plant tissue. These involve the addition of effective amounts of selected amino acids, their derivatives or combinations of these as a source of reduced nitrogen, together with an optimum auxin dosage to the nutritive media used to regenerate or maintain the embryonic tissue. A synergistic effect is found by adding these amino acids either in combination or in combination with ammonium ion together with the selected auxin dosage.

10 Claims, 1 Drawing Sheet

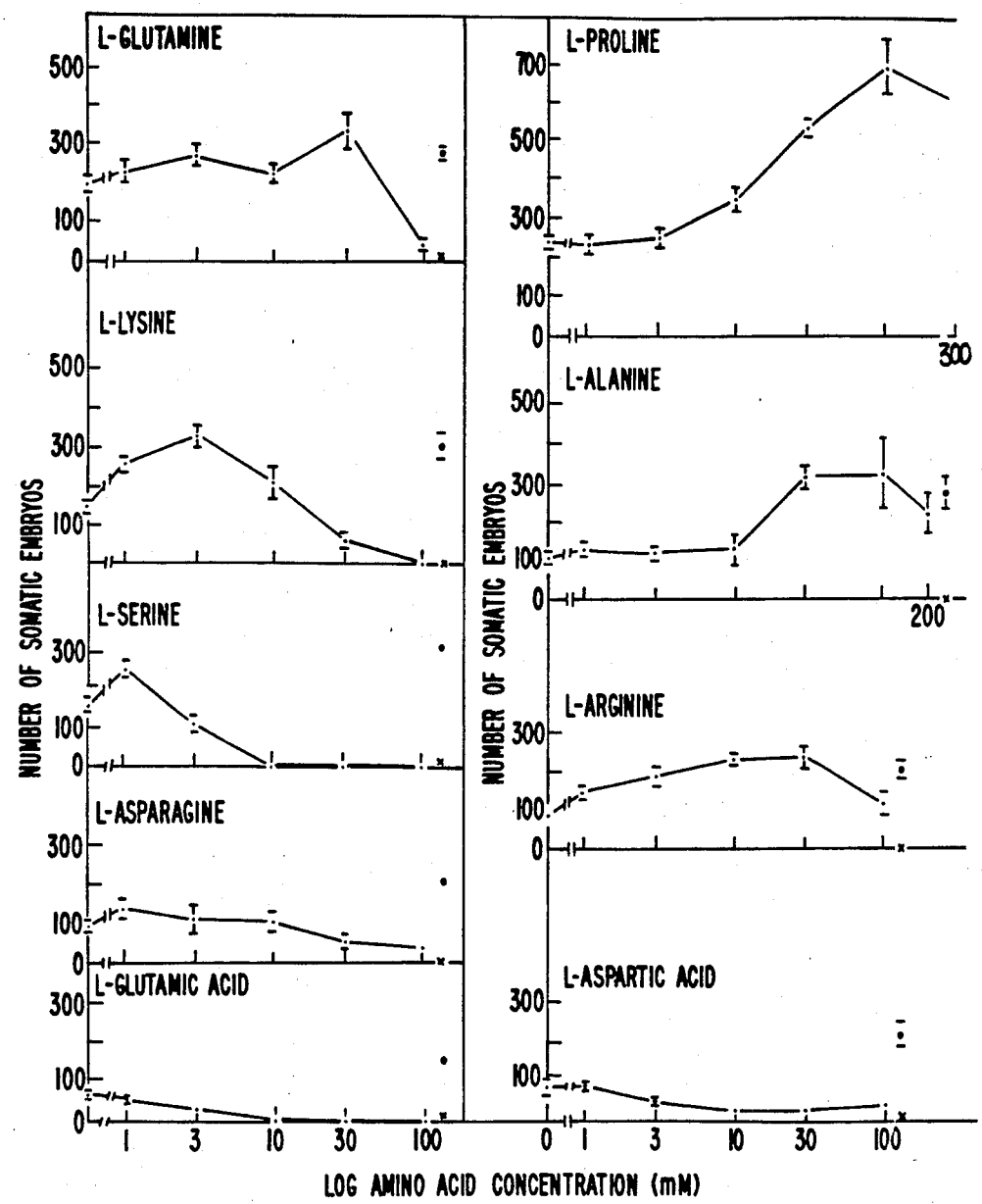
FIG.—I.

METHODS AND MATERIALS FOR ENHANCED SOMATIC EMBRYO REGENERATION IN THE PRESENCE OF AUXIN

RELATED APPLICATIONS

This is a continuation of application Ser. No. 504,891, filed June 16, 1983, which is a continuation-in-part of application Ser. No. 496,186, filed May 19, 1983.

TECHNICAL FIELD

This invention relates to the culturing of embryonic plant tissue and more specifically to improved methods and materials to increase the quantity of embryos produced from somatic tissue by culturing in optimal reduced nitrogen and auxin.

BACKGROUND ART

It has been recognized that recent progress in genetic engineering offers plant breeders the ability to avoid the delay in crop improvement inherent in classical breeding techniques. However, there remains a difficulty in application of these techniques, for unicellular and multicellular organisms require different techniques to change the entire genetic makeup. In microorganisms, one attempts to effect change at the cellular level with confidence that this will be reproduced through succeeding generations.

In organisms which are not normally unicellular, such as plants, it is advantageous to perform genetic manipulations at the cellular level, then regenerate and raise a mature plant expressing the new characteristics. The cloning of plants by asexual means offers advantages to plant breeders which cannot be obtained using sexual means of reproduction. Sexual reproduction necessitates the recombination of traits or characters in such a way that often, the sib generation loses the properties of its parents. Cloning of plants allows the breeder to reproduce and expand the numbers of individuals all of which have the same genetic make-up.

Plants can be cloned by a variety of methods other than somatic embryogenesis such as by cuttings, air layering, tuber and close division and in vitro micropropagation. All of these methods are labor intensive and may be economically disadvantageous for some applications. Cloning by somatic embryogenesis can offer high numbers of clones (20,000 to 40,000 units per gram fresh weight input) and low cost since embryos can be produced in batch suspension culture and handled automatically in a fluid medium.

In vitro cultivation of plant tissue requires that the tissue be maintained in a medium which provides nutrition and sustains viability. This tissue maintenance can be promoted in plant organ, tissue or cell cultures.

In culture, plant cells are typically induced to undergo repeated cell divisions on a nutritive substrate, producing an amorphous cell mass known as callus. The callus can be maintained through subculture to allow mass proliferation. The callus may also be induced to undergo differentiation which results in the organized tissues and organs of the mature plant.

In this manner, genetic changes may be effected on a cellular level and then maintained through subsequent development to produce an entire crop with identical genetic characteristics. This allows the plant breeder to bypass the normal genetic barriers in plant reproduction, and obtain a more uniform and advantageous field crop.

Somatic embryogeneis can be accomplished in numerous plant species. Examples of plants capable of somatic embryogenesis are cited in Evans, D. A. et al., "Growth and Behavior of Cell Cultures: Embryogenesis and Organogenesis" in *Plant Tissue Culture: Methods and Applications in Agriculture*, T. A. Thorpe, Ed., Academic Press, pg. 45 et seq. (1981). These examples are not exhaustive; reports of new species capable of somatic embryogenesis appear weekly.

Technology reviews on somatic embryogenesis have outlined methods which enable production of somatic embryos (see Kohlenback, H. W., "Comparative Somatic Embryogenesis," in Frontiers of Plant Tissue Culture, T. A. Thorpe, pg, 59 et. seq., Int. Plant Tissue Cult. Congress, Calgary, CN. (1978); Sharp et al. "The Physiology of in vitro Asexual Embryogenesis" Hortic. Reviews 2, 268–310 (1982)). One parameter which is necessary for embryogenesis from somatic cell cultures is a pretreatment with an auxin. One auxin which is generally used in 2,4-dichlorophenoxyacetic acid (2,4-D) although this is by no means to only auxin which can be utilized. A detailed investigation of auxin activity for carrot somatic embryogenesis has been done by Kamada, H. and H. Harada "Studies on the Organogenesis in Carrot Tissue Culture. I. Effects of Growth Regulators on Somatic Embryogenesis and Root Formation." Zeit. Pflanzenphysiol. 91, 255. 1979, and in alfalfa by Walker, K. A. et al., "Initiation of Sexual Embryogenesis in Somatic Cell Cultures," Tissue Culture Assn. Meeting Abstracts, No. 68, (1980) and Walker, K. A. et al., "Organogenesis in Callus Tissue of *Medicago sativa*. The Temporal Separation of Induction Processes from Differentiation Processes," Plant Sci. Lett. 16, 23–30 (1979).

Some techniques exist for increasing the quantity of the embryonic cells obtained through tissue culture of plant somatic tissue. A requirement for a source of reduced nitrogen for the formation of in vitro somatic embryos has been recognized in carrot cells cultures. This effect has since been confirmed and extended to a variety of other species. A detailed study of this reduced nitrogen requirement may be found in Walker, K. A. and S. J. Sato "Morphogenesis in Callus Tissue of *Medicago sativa*: "The Role of Ammonium Ion in Somatic Embryo Genesis," Plant Cell Tissue Organ Culture, 1: 109–21.

It has also been recognized that certain amino acids will stimulate somatic embryogenesis in carrot cell cultures. Wetherell, D. F. and D. K. Dougall "Sources of Nitrogen Supporting Growth in Embryogenesis in Cultured Wild Carrot Tissue," Physiol. Plant. 37: 97–103 and Kamada, H. and H. Harada, "Studies on the Organogenesis in Carrot Tissue Cultures II, Effects of Amino Acids and Inorganic Nitrogenous Compounds on Somatic Embryogenesis", Z. Pflanzenphysiol. 91: 453–463. (1979). However, previous studies have either lacked sufficient control treatments to allow comparison to other experimental treatments or they are limited to a small range of concentrations which so not test for optimization.

The auxin studies previously cited have defined three parameters which interact in the induction of embryogenesis by auxin. These are: (1) auxin structure; (2) auxin concentration; and (3) time of exposure. For example, Kamada and Harada find that auxin structure determines potency in affecting differentiation in cell culture. The lower the concentration threshold for auxin-induced differentiation, the higher the potency. The reported order of decreasing potency for auxin for somatic embryogenesis in carrot was 2,4,5-trichlorophenoxyacetic acid=m-chlorophenoxyacetic acid>2,4-dichlorophenoxyacetic acid>p-chlorophenoxyacetic acid>α-naphthylene acetic acid=indole-3-acetic acid>indole-3-butyric acid. Differences in potency due to auxin structure can be compensated for by adjusting auxin concentration to achieve comparable regeneration. Likewise, time of exposure to a given auxin structure at a given concentration is a critical for efficient regeneration. The product of auxin structure, auxin concentration and time of exposure will be referred to hereafter as dosage (dose) of auxin or auxin dosage (dose).

A dosage of auxin usually precedes somatic embryogenesis from cell culture. Embryo differentiation occurs when cells grown at one auxin dosage (primary dosage) are either subcultured on medium containing a lower auxin dosage or no auxin, or treated by other methods which decrease auxin dosage (see Kohlenbach review). Continued exposure of cells to the primary auxin dosage is not recommended by numerous authors (Phillips and Collins, Crop Sci., 20, 323, 1980; Kohlenbach (1978) as before; Sharp et al. (1980) as before, Reinert, J. and M. Tazawa, Planta 87, 239, 1969 and Halperin, W. Science 146, 408, 1964) as embryo regeneration is disrupted by these dosages.

Another factor which enables embryogenesis from somatic cell cultures is the addition of reduced nitrogen to the culture medium. This nitrogen requirement can be fulfilled by ammonium, a variety of L-amino acids, or combinations of all of these (Halperin, W. and D. F. Wetherell, Nature 205, 519-1965; Wetherell, D. F. and D. K. Dougall, Physiol. Plant 37, 97-1976; Kamada, H. and H. Harada. Z. Pflanzenphysiol. 91, 453 (1979). This requirement for reduced nitrogen can be supplied prior to auxin removal or decrease in auxin dosage (Halperin, W. Amer. J. Bot. 53, 443. 1966) or in the regeneration medium containing no or reduced auxin dosage. This yields high frequency and high quality embryos of asexual origin.

Several authors have recognized that auxin and ammonium ion interact in somatic embryogenesis (Sharp et al. (1980), Halperin, Am. J. Bot. 53: 443–453 1966, Caldas, L. S. Effects of various growth hormones on the production of embryoids from tissue culture of the wild carrot, *Daucus carota* L., Ph.D. dissertation, Ohio State Univ., 1971). These authors recommend against the use of 2,4-D or other auxins as an additive to plant regeneration medium. Sharp et al. (1980) point out that ammonium ion may merely permit somatic embryogenesis to occur after pretreatment with higher auxin dosages.

It is an object of this invention to provide methods and materials to increase the quantity of somatic embryos produced from plant tissue.

It is a further object of this invention to provide optimized sources of reduced nitrogen in combination with auxins for regeneration of somatic embryos.

It is yet another object of this invention to provide methods and materials allowing mass propagation of numerous species of plants through somatic embryogenesis.

It is a still further object of this invention to provide methods and materials for a generation of numerous viable somatic embryos with identical genetic and phenotypic traits.

DISCLOSURE OF THE INVENTION

This invention provides novel and improved methods and materials for producing numerous somatic embryos from plant tissue by the addition of optimal amounts of amino acids and sources of reduced nitrogen to regeneration media containing optimal auxin dosages.

BEST MODE FOR CARRYING OUT THE INVENTION

In this invention we provide methods and materials for enhancing the quantity of somatic embryos produced from plant somatic tissue derived from species which are capable of somatic embryogenesis.

Numerous important crop and horticultural species have been shown to be capable of propagation through tissue culture and somatic embryogenesis. These varieties include, but are not limited to:

TABLE 1

| Vegetable crops | Fruit and nut trees |
|---|---|
| alfalfa | almond |
| asparagus | apple |
| beet | banana |
| brussels sprouts | coffee |
| carrot | date |
| cauliflower | grapefruit |
| eggplant | lemon |
| onion | olive |
| spinach | orange |
| sweet potato | peach |
| tomato | Bulbs |
| Fruit and berries | lily |
| blackberry | daylily |
| grape | Easter lily |
| pineapple | hyacinth |
| strawberry | Flowers |
| Foliage | African violet |
| silver vase | chrysanthemum |
| begonia | gerbera daisy |
| crytanthus | gloxinia |
| dieffenbachia | petunia |
| dracaena | rose |
| eiddleleaf | orchid |
| pointsettia | Silviculture (forestry) |
| weeping fig | douglas fir |
| rubber plant | pine |
| Pharmaceutical | quaking aspen |
| atropa | redwood |
| ginseng | rubber tree |
| pyrethium | |
| Ferns | |
| Australia tree fern | |
| Boston fern | |
| Maidenhair fern | |
| rabbitsfoot fern | |
| staghorn fern | |
| sword fern | |
| Cereal Grains | |
| barley | |
| corn | |
| millet | |
| wheat | |

For a more exhaustive list of species capable of somatic embryogenesis, see Evans, D. A. et al., "Growth and Behavior of Cell Cultures: Embryogenesis and Organogenesis" in Plant Tissue Culture: Methods and Applications in Agriculture, Thorpe, ed., Acamdemic Press, page 45 et. seq. (1981).

In alfalfa, embryogenesis can be routinely induced in the Regen S line of Saunders and Bingham, "Production of Alfalfa Plants from Callus Tissue," Crop Sci., 12: 804-808 (1972).

Plants of *Medicago sativa* cultivar Regen S derived from the second cycle recurrent selection for regeneration from the cross of the varieties Vernal and Saranac were used. Callus was initiated by surface sterilizing petioles with 50% Clorox ® for five minutes, washing with $H_2O$ and plating on Shenk-Hildebrandt medium (SH), Shenk, R. V. and A. C. Hildebrandt, Can. J. Bot., 50: 199-204 (1972). The medium contained 25 μM α-naphthyleneacetic acid and 10 μM kinetin (termed maintenance medium). Callus which formed on the explant tissue was separated from the remaining uncallused tissue and repeatedly subcultured on maintenance medium. Callus was subcultered at 3 week intervals and grown under indirect light at 27° C.

Three to nine grams of callus was collected at 17 and 24 days post-subculture from plates of maintenance medium and transferred to 100 ml of liquid SH containing 50 μM 2,4-dichlorophenoxyacetic acid (2,4-D) and 5 μM kinetin (B) for induction. Walker, K. A., M. L. Wendeln and E. G. Jaworski, Plant Sci. Lett. 16: 23-30. (1979). Cells were cultured in 500 ml flasks for 3 days at 27° C. on an orbital shaker at 100 R.P.M. under indirect light.

Induced cells were aseptically sized on a series of column sieves under gentle vacuum. Cell clumps either fell or were forced at 20 mesh (820 μm) and collected on a 60 mesh (230 μm) through stainless steel screen. Cells retained on the 60 mesh screen were washed with 500 ml of SH minus hormone liquid medium for every 100 ml of induction culture volume. The washing medium was also removed by vacuum. The fresh weight of the cell clumps was taken and cells were resuspended in SH medium without hormones at 150 mg fresh weight per ml. Seventy-five mg (0.5 ml) of resuspended cells were pipeted onto approximately 10 ml of agar solidified medium in 60 mm×15 mm petri dishes.

Alternatively, somatic embryogenesis in suspension culture will occur if 300 mg (2 ml) of resuspended cells are delivered to 8 ml of liquid SH medium contained in a 50 ml erlenmeyer flask. The embryogenesis media contained SH medium ($NH_4^+$ equal to 2.6 mM) with 3% (w/v) sucrose without hormones. Ammonium ion free medium was made by substituting an equivalent amount of $NaH_2PO_4$ for the $NH_4H_2PO_4$ of SH. The 25 mm $NH_4^+$ control medium consisted of ammonium free medium supplemented with 12.5 mM $(NH_4)_2SO_4$. All organic and inorganic sources of reduced nitrogen and 2,4-D were sterilized by 0.2 μm filtration and subsequently added to freshly autoclaved medium.

Each treatment was generally plated in 10 replicates. Dishes were parafilm wrapped and incubated for 21 days. Suspension flasks were foam plugged, sealed with Saran Wrap ® and incubated for 14 days on an orbital shaker at 100 rpm. Incubation was at 27° C. under 12 hours illumination from cool white fluorescent tubes at 28 cm from solidified cultures or 2 μm from suspension cultures.

Embryogenesis was visually measured after incubation by counting green centers of organization on the callus using a steroe microscope at a magnification of 10×.

Embryo size was measured using a calibrated ocular scale at 10× magnification. Embryo shape was determined by visual examination. Conversion of embryos to whole plants with root and shoot axis (first primary leaf) was done by aseptically transferring embryos from amino acid treatments at 21 days of initial culture to half-strength SH medium supplemented with 25 μM gibberelic acid and 0.25 μM α-naphthyleneacetic acid solidified with 0.8% agar.

All protein amino acids were tested at between 1 and 100 mM concentrations. Two response types emerged from this initial screen and based on these results further tests with sieved cells were performed. Table 2 excludes amino acids of the first response type, those which were found to be toxic to growth or inhibitory to embryogenesis compared to the SH-medium (2.6 mH $NH_4^+$) control. These amino acids included the sulfur and aromatic and most of the branched chain family. None of these amino acids stimulated embryo-genesis over the SH medium control and all were toxic, in that they inhibited growth or caused browning of the callus either at 1 or 10 mM.

The second response type from the initial screen either stimulated embryogenesis or caused an increase in embryo size when compared to the SH control. See Table 2. Detailed concentration dependence studies were performed on these amino acids and the results are shown in FIG. 1. The amino acid most effective in stimulating somatic embryo formation was proline, which yielded nearly 3-fold more embryos than the 2.6 mM $NH_4^+$ control and was twice as effective as 25 mM $NH_4^+$, the optimal ammonium concentration in alfalfa (D). (Walker, et al., supra). Alanine, arginine, glutamine and lysine were all less effective but stimulated embryo formation to approximately the level of 25 mM $NH_4^+$. Serine and asparagine showed less stimulation of embryogenesis compared to the SH control, but increased embryo size.

Table 2 summarizes the amino acids and other nitrogen sources which have been found to be stimulatory to somatic embryogenesis in alfalfa. It is important to note that the ester and amide forms of proline are highly active in stimulating embryo numbers and quality as is the dipeptide, prolyl alanine. It is interesting to note that the nonprotein amino acid ornithine is also acitve.

TABLE 2

| The Effect of Reduced Nitrogen Sources on Somatic Embryogenesis in Alfalfa |
|---|
| Stimulatory Sources |
| Ammonium |
| Proline |
| Alanine |
| Glutamine |
| Arginine |
| Asparagine |
| Ornithine |
| Serine |
| Lysine |
| L-proline amide |
| L-prolyl-L-alanine |
| L-proline methyl ester |

Using the techniques described above, embryo quality was measured by visual inspection of the embryo size. The data is presented in Table 3.

TABLE 3

| Effect of Reduced Nitrogen Treatment on Somatic Embryo Size | | |
|---|---|---|
| Treatment | Length | Width |
| Control (25 mM $NH_4^+$) | 0.805 ± 0.084 | 0.383 ± 0.019 |
| 100 mM L-Proline | 1.143 ± 0.081 | 0.867 ± 0.046 |
| 30 mM L-Alanine | 1.163 ± 0.090 | 0.744 ± 0.037 |
| 100 mM L-Alanine | 1.192 ± 0.102 | 0.833 ± 0.049 |
| 30 mM L-Arginine | 1.521 ± 0.142 | 0.663 ± 0.048 |
| 30 mM L-Glutamine | 1.342 ± 0.122 | 0.773 ± 0.051 |
| 3 mM L-Lysine | 1.163 ± 0.096 | 0.652 ± 0.039 |

TABLE 3-continued

Effect of Reduced Nitrogen Treatment on Somatic Embryo Size

| Treatment | Length | Width |
|---|---|---|
| 3 mM L-Asparagine | 0.699 ± 0.062 | 0.446 ± 0.027 |
| 10 mM L-Asparagine | 1.239 ± 0.102 | 0.610 ± 0.034 |

Based on the data of Table 2 and Table 3 we can rank the effectiveness of the amino acid additives in improving embryo size in the following order:

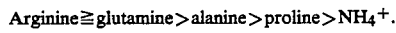

Arginine ≧ glutamine > alanine > proline > $NH_4^+$.

Using the techniques described above, the conversion of embryos to whole plants with root and shoot axis (first primary leaf) was observed and tabulated. The results are as follows:

TABLE 4

Conversion of Somatic Embryos to Alfalfa Plantlets

| Initial Treatment | % Plants with First Primary Leaf |
|---|---|
| 25 mM $NH_4^+$ | 33.3% ± 4.2 |
| 100 mM L-Proline | 54.0% ± 6.4 |
| 50 mM L-Alanine | 63.5% ± 4.4 |
| 30 mM L-Arginine | 59.0% ± 6.2 |
| 30 mM L-Glutamine | 67.0% ± 3.4 |

Based on the data of Table 4, the effectiveness of an additive on the conversion of embryos to plantlets is as follows:

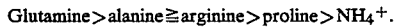

Glutamine > alanine ≧ arginine > proline > $NH_4^+$.

From the correlation between these sets of data it is shown that embryo size is a good indicator of embryo conversion to plantlets and thus a good indicator of the quality of embryos produced by a given technique.

The optimal amounts of added amino acids were determined for the stimulation of somatic embryogenesis on both agar solidified cultures and liquid suspension cultures. These data are presented in Tables 5 and 6 as follows:

TABLE 5

Stimulation of Somatic Embryogenesis by Reduced Nitrogen Sources on Agar Solidified Cultures of Alfalfa

| Source | % Stimulation | Concentration Range (in mM) | Optimum Concentration |
|---|---|---|---|
| Control (2.6 mM $NH_4^+$) | 100 | | |
| L-Proline | 330 | 30 to 300 | (100) |
| L-Alanine | 314 | 20 to 150 | (75-100) |
| L-Glutamine | 175 | 20 to 50 | (30-40) |
| L-Arginine | 244 | 5 to 50 | (30-40) |
| L-Asparagine | 155 | 0.5 to 3 | (1) |
| L-Ornithine | 156 | 1 to 3 | (1-3) |
| L-Serine | 160 | 0.5 to 2 | (1) |
| L-Lysine | 233 | 1 to 10 | (3) |
| L-Proline amide | 240 | 30 to 200 | (50-100) |
| L-Proline methyl ester | 241 | 5 to 25 | (10) |
| L-Prolyl-L-alanine | 210 | 30 to 200 | (50-100) |

TABLE 6

Stimulation of Somatic Embryogenesis by Reduced Nitrogen Sources in Liquid Suspension Cultures of Alfalfa

| Source | % Stimulation | Concentration Range (in mM) | Optimum Concentration (in mM) |
|---|---|---|---|
| Control (2.6 mM $NH_4^+$) | 100 | | |
| L-Proline | 528 | 30 to 300 | (100) |
| L-Alanine | 240 | 25 to 200 | (50) |
| L-Glutamine | 243 | 5 to 75 | (50) |
| L-Arginine | 168 | 5 to 75 | (50) |
| L-Lysine | 180 | 1 to 10 | (3) |

AMINO ACID INTERACTION WITH AMMONIUM ION

Cells were induced, sieved and plated as in the above experiments. The concentrations of proline or arginine and $NH_4^+$ were varied to determine if the optimum concentration for any additive alone was influenced by the presence of the additional additive.

1. Proline: Proline was tested over a range of 30 mM to 300 mM where the amount of added $NH_4^+$ varied between 0 and 25 mM. The results are indicated in Table 7.

2. Arginine: A similar experiment where the concentration of arginine was varied in addition to the concentration of $NH_4^+$ added to the medium. The results are shown in Table 7.

TABLE 7

Effect of Amino Acid Interaction with Ammonium Ion in Alfalfa (mean number of embryos produced in at least seven trials)

| | Proline Concentration (mM) | | |
|---|---|---|---|
| | 30 | 100 | 300 |
| $NH_4+$ Concentration (mM) | | | |
| 0 | 326 | 470 | 133 |
| 1.0 | 502 | 747 | 541 |
| 2.6 | 753 | 731 | 825 |
| 10.0 | 887 | 811 | 572 |
| 25.0 | 744 | 1,042 | 844 |

| | Arginine Concentration (mM) | | | |
|---|---|---|---|---|
| | 0 | 10 | 30 | 100 |
| $NH_4+$ Concentration (mM) | | | | |
| 0 | 12 | 147 | 126 | 99 |
| 1.0 | 70 | 252 | 246 | 157 |
| 2.6 | 207 | 298 | 306 | 264 |
| 10.0 | 340 | 408 | 411 | 311 |
| 25.0 | 335 | 297 | 233 | 148 |

It is seen in each case that a synergistic effect resulted when the optimum amounts of arginine or proline and optimum amounts of $NH_4^+$ were added.

COMBINATIONS OF AMINO ACIDS

The following Table shows the effect of adding combinations of amino acids to alfalfa cultures in the absence of $NH_4^+$. Combinations of amino acids have a synergistic effect on embryo numbers and quality.

TABLE 8

| | | Embryo Number |
|---|---|---|
| Expt. 1 | 50 mM L-Proline | 80 |
| | 30 mM L-Glutamine | 50 |
| | Proline and Glutamine | 248 |
| Expt. 2 | 100 mM L-Proline | 27 |
| | 100 mM L-Alanine | 74 |
| | 100 mM L-Proline + 50 mM L-Alanine | 215 |

TABLE 8-continued

| | Embryo Number |
|---|---|
| 30 mM L-Arginine | 135 |
| 100 mM Proline + 30 mM Arginine | 215 |

CELERY EMBRYOGENESIS

Seeds of celery *Apium graveolens* (variety Calmario) were germinated for one to two weeks. The resulting seedlings were sterilized with a solution of 10% Clorox ® for 20 minutes. Cotyledons or hypocotyls were removed and explants were placed on 0.8% agar solidified Shenk and Hildebrandt (SH) medium containing 25 μM 2,4-D and 5 μM benzyladenine. After initiation of callus (3-4 weeks), callus was transferred to SH medium with 2.5 μM 2,4-D and 0.5 μM benzyladenine. Heat labile additives were filter sterilized and added to warm medium. When required, specific amounts of tissue for innoculation were obtained using a modified spatula device and filling this to uniform volume. Subsequent subcultures of callus were on SH medium plus 1 μM picloram and 0.5 μM benzyladenine. For somatic embryo production 75 mg of callus cells was transferred to 0.8% agar solidified SH medium containing filter sterilized additives and incubated for 18 to ;b 30 days at 24° C. under the same conditions as alfalfa.

EFFECTS OF REDUCED NITROGEN SOURCES ON CELERY REGENERATION

Amino acids proline, alanine and glutamine were compared against $NH_4^+$ control-treated embryos.

Treating cultures with 50 mM alanine resulted in higher frequency embryogenesis than all other treatments, as well as embryos which had better cotyledons, root and primary leaf development than other cultures. The following order of total embryo numbers formed was observed:

50 mM alanine > 50 mM proline > 25 mM glutamine-N > 25 mM $NH_4^+$.

Although proline stimulated embryogenesis better than glutamine, the latter resulted in better development of seedling-like embryos. Ammonium treated cultures developed smaller and fewer embryos than all other treatments. Glutamic acid, when added singly to celery regeneration medium at 30 mM, stimulates embryo number in celery compared to 25 mM $NH_4^+$-treated material. Alanine, proline, glutamine and glutamate at the above concentrations improve celery embryo conversion to plantlets compared to $NH_4^+$ treated embryos.

AUXIN DOSAGE

The cell culture transfer experiment was performed by overlaying agar solidified medium with a 5.4 cm disc of Whatman ® No. 1 filter paper which had been previously sterilized. Suspensions of induced cells were delivered and spread as usual on the filter paper surface. Transfer of the cells was accomplished by aseptically moving the disc and cells to the surface of a new plate of medium.

An experiment was performed to determine whether somatic embryogenesis in alfalfa was inhibited by including high dosages of auxin (here, 2,4-D at 10 and 30 μM) in the regeneration medium. This information would be useful for the synchronization of embryogenesis. Table 9 shows the results of this experiment where proline and alanine were included in the regeneration medium in addition to 2,4-D. Rather than inhibiting somatic embryogenesis the 2,4-D stimulated embryogenesis in the presence of SH medium (10 μM, 2,4-D) and also stimulated embryogenesis in SH medium supplemented with L-proline or L-alanine (at 30 μM 2,4-D).

TABLE 9

Interactive effect of $NH_4^+$, Proline and Alanine with 2,4-D on somatic embryogenesis in alfalfa on solid medium.

| | No. of Somatic Embryos ± SEM | Relative % of Control |
|---|---|---|
| SH (2.6 mM $NH_4^+$) | 83 + 08 | 100% |
| SH + 10 uM 2,4-D | 153 + 14 | 184% |
| SH + 30 uM 2,4-D | 63 + 10 | 76% |
| SH + 50 mM proline | 350 + 34 | 100% |
| SH + 50 mM proline + 30 uM 2,4-D | 567 + 32 | 162% |
| SH + 50 mM alanine | 150 + 19 | 100% |
| SH + 50 mM alanine + 30 uM 2,4-D | 254 + 25 | 169% |

TABLE 10

Optimization of the 2,4-D concentration in the regeneration medium during embryogenesis. In the regeneration in the presence of 100 mM L-Proline, 50 mM L-Alanine and 25 mM $NH_4^+$ on solid medium.

| Reduced Nitrogen Source | No. of Somatic Embryos + S.E.M. 2,4-D Concentration (uM) | | | | | | |
|---|---|---|---|---|---|---|---|
| | 0 | 1 | 3 | 10 | 30 | 100 | 300 |
| 25 mM $NH_4^+$ | 55 ± 11 | 137 ± 17 | 92 ± 12 | 129 ± 12 | 86 ± 6 | 0 ± 0 | 0 ± 0 |
| 100 mM Proline | 413 ± 39 | 424 ± 44 | 557 ± 57 | 703 ± 48 | 606 ± 65 | 669 ± 24 | 107 ± 8 |
| 50 mM Alanine | 142 ± 22 | 223 ± 25 | 329 ± 31 | 391 ± 31 | 473 ± 54 | 239 ± 23 | 49 ± 4 |

Optimization of the 2,4-D concentration versus three reduced nitrogen sources is shown in Table 10. Embryogenesis in the presence of 25 mM $NH_4^+$ is enhanced by 2,4-D over the range of 1 to 30 μM. Comparing Table 9 and 10 indicates that increasing the $NH_4^+$ concentration from 2.6 mM (that level found in SH basal medium) to 25 mM increases the range of effective maximal 2,4-D dosage from 10 to 30 μM. Somatic embryogenesis in proline- or alanine-supplemented regeneration medium is enhanced over the range of 1 to 100 μM 2,4-D. Thus, in the presence of these amino acids, auxin dosage can be increased above the level of the induction medium (50 μM 2,4-D) without inhibiting somatic embryogenesis. These results also demonstrate that the quality ($NH_4^+$ versus amino acids) and quantity (low $NH_4^+$ versus high $N_4^+$) interact with 2,4-D to stimulate somatic embryogenesis during embryo regeneration. Thus, "reduced nitrogen dosage," the product of reduced nitrogen quality and quantity evolves as a concept from these observations.

Similar interactive effects of 2,4-D and a reduced nitrogen source (here proline) can be seen where embryo-genesis occurs in liquid suspension culture (see Table 11). Stimulation of embryogenesis in liquid culture with 2,4-D occurs at and between 1 to 100 µM.

TABLE 11

Embryogenesis in the presence of SH + 83 mM L-Proline and various concentration of 2,4-D in liquid suspension culture.

| 2,4-D Concentration (uM) | Somatic Embryo Number ± SEM |
|---|---|
| 0 | 310 + 63 |
| 1 | 401 + 50 |
| 3 | 414 + 45 |
| 10 | 327 + 45 |
| 100 | 314 + 67 |
| 300 | 2 + 02 |

TABLE 12

The effect of medium transfer and 2,4-D supplementation on somatic embryogenesis on solid medium.

| First Medium | Second Medium | Transfer Time | No. of Somatic Embryos ± SEM |
|---|---|---|---|
| SH + 100 mM Proline | — | (No transfer) | 479 + 28 |
| SH + 100 mM Proline | SH + 100 mM Proline | 2 days | 116 + 18 |
| SH + 100 mM Proline | SH + 100 mM Proline + 3 uM 2,4-D | 2 days | 508 + 53 |

In addition to stimulating gross numbers of embryos (Table 9-11), 2,4-D supplements have found use in overcoming decreased embryogenic potential when the culture medium is changed (Table 12). Embryo numbers decreased as a consequence of transferring cells to fresh medium. Including 3 µM 2,4-D in the second medium fully restores embryogenesis to the level obtained in the treatment which was not transferred. This technique is significant since the timing of culture additions and replenishment of medium constituents may be necessary for the production of high frequency and high quality somatic embryos.

Although the foregoing invention has been described in some detail by way of illustration and example for purposes of clarity of understanding, it will be obvious to one skilled in the art that certain changes and modifications may be practiced within the scope of the appended claims.

We claim:

1. A method of producing embryonic tissue from Leguminosae somatic tissue wherein somatic tissue is regenerated from induced cells in a nutritive plant cell culture medium to form embryonic tissue, said method comprising:

providing a nutritive plant cell culture medium upon which somatic embryos differentiate from induced cells, said medium including auxins at a final medium concentration between 1 and 100 µM, together with a sufficient amount of at least one reduced nitrogen source selected from the group consisting of ammonium salts at a final medium concentration between 1 and 25 mM and amino acids at a final medium concentration between 0.5 and 300 mM, said nutritive culture medium upon which somatic embryos differentiate resultantly providing an increased number of somatic embryos, as compared to the number of somatic embryos produced in a plant cell culture without said combination of auxins and at least one reduced nitrogen source in a single medium;

exposing undifferentiated Leguminosae somatic tissue to said provided nutritive plant cell culture medium including sufficient amounts of auxin between 1 and 100 µM and said at least one reduced nitrogen source, to cause embryogenesis in said Leguminosae somatic tissue to form somatic embryos; and, sustaining said somatic embryos on said provided nutritive plant cell culture medium including sufficient amounts of auxin between 1 and 100 µM and said at least one reduced nitrogen source, to thereby permit embryo development into plantlets.

2. A method as recited in claim 1 wherein said auxin comprises 2,4-dichlorophenoxyacetic acid at a final nutritive culture medium concentration of 1-100 µM.

3. A method as recited in claim 1 wherein said sufficient amount of at least one reduced nitrogen source comprises at least one amino acid at a final nutritive culture medium concentration selected from the group consisting of:

(a) proline at 30-300 mM;
(b) alanine at 20-200 mM;
(c) arginine at 15-75 mM;
(d) glutamine at 15-75 mM;
(e) lysine at 1-10 mM;
(f) asparagine at 0.5-3 mM;
(g) serine at 0.5-2 mM;
(h) ornithine at 1-3 mM;
(i) glutamate at 10-50 mM;
(j) L-proline amide at 30-200 mM;
(k) L-proline methyl ester at 5-25 mM; and
(l) L-prolyl-L-alanine at 30-200 mM.

4. A method as recited in claim 1 wherein said at least one reduced nitrogen source consists of both amino acid and ammonium salts, in said provided nutritive culture medium, thereby resultantly providing an increased number of somatic embryos, compared to the number of somatic embryos obtained in a plant nutritive cell culture without said ammonium salts.

5. A method in accordance with claim 1 wherein the Leguminosae somatic tissue is derived from *Medicago sativa* L.

6. A nutritive plant cell culture medium used for the induction of somatic embryonic tissue, or the regeneration or development of plant somatic embryonic tissue, comprising:

a medium having a source of ammonium ion;
an addition to said medium of at least L-lysine, its amide, alkyl ester or dipeptidyl derivatives added in an amount sufficient to provide a final concentration of L-lysine in said medium of approximately 1 to 10 mM; and,
at least one auxin in an amount sufficient to provide a final auxin concentration in said medium of 1 to 100 µM.

7. A nutritive plant cell culture medium used for the induction of somatic embryonic tissue, regeneration or development of plant somatic embryonic tissue, comprising:

a medium having a source of ammonium ion;
an addition to said medium of at least L-serine, its amide, alkyl ester or dipeptidyl derivatives added in an amount sufficient to provide a final concentration of L-serine in said medium of approximately 0.5 to 2 mM; and,
at least one auxin in an amount sufficient to provide a final auxin concentration in said medium of 1 to 100 µM.

8. A nutritive plant cell culture medium used for the induction of somatic embryonic tissue, regeneration or development of plant somatic embryonic tissue, comprising:
  a medium having a source of ammonium ion;
  an addition to said medium of at least L-ornithine, its amide, alkyl ester or dipeptidyl derivatives added in an amount sufficient to provide a final concentration of L-ornithine in said medium of approximately 1 to 3 mM; and,
  at least one auxin in an amount sufficient to provide a final auxin concentration in said medium of 1 to 100 $\mu$M.

9. A nutritive plant cell culture medium used for the induction of somatic embryonic tissue, regeneration or development of plant somatic embryonic tissue, comprising:
  a medium substantially free of ammonium ion;
  an addition to said medium of at least L-lysine, its amide, alkyl ester or dipeptidyl derivatives added in an amount sufficient to provide a final concentration of L-lysine in said medium of approximately 1 to 10 mM; and,
  at least one auxin in an amount sufficient to provide a final auxin concentration in said medium of 1 to 100 $\mu$M.

10. A nutritive plant cell culture medium used for the induction of somatic embryonic tissue, regeneration or development of plant somatic embryonic tissue, comprising:
  a medium substantially free of ammonium ion;
  an addition to said medium of at least L-ornithine, its amide, alkyl ester or dipeptidyl derivatives added in an amount sufficient to provide a final concentration of L-ornithine in said medium of approximately 1 to 10 mM; and,
  at least one auxin in an amount sufficient to provide a final auxin concentration in said medium of 1 to 100 $\mu$M.

* * * * *